US012345702B2

(12) United States Patent
Smith et al.

(10) Patent No.: US 12,345,702 B2
(45) Date of Patent: Jul. 1, 2025

(54) ON-SITE DETECTION OF PARASITIC INFECTION OF MAMMALS

(71) Applicant: TECHNOLOGICAL UNIVERSITY DUBLIN, Dublin (IE)

(72) Inventors: Sean Smith, Dublin (IE); Tara McElligott, Dublin (IE); Jose Lopez Escobar, Dublin (IE); Daniel Izquierdo Hijazi, Dublin (IE)

(73) Assignee: TECHNOLOGICAL UNIVERSITY DUBLIN, Dublin (IE)

( * ) Notice: Subject to any disclaimer, the term of this patent is extended or adjusted under 35 U.S.C. 154(b) by 991 days.

(21) Appl. No.: 17/413,744

(22) PCT Filed: Dec. 11, 2019

(86) PCT No.: PCT/EP2019/084770
§ 371 (c)(1),
(2) Date: Jun. 14, 2021

(87) PCT Pub. No.: WO2020/120640
PCT Pub. Date: Jun. 18, 2020

(65) Prior Publication Data
US 2022/0057385 A1   Feb. 24, 2022

(30) Foreign Application Priority Data
Dec. 13, 2018   (GB) ..................... 1820327

(51) Int. Cl.
*G06T 7/00* (2017.01)
*A61B 10/00* (2006.01)
(Continued)

(52) U.S. Cl.
CPC ..... *G01N 33/5091* (2013.01); *A61B 10/0038* (2013.01); *B01L 3/502* (2013.01);
(Continued)

(58) Field of Classification Search
CPC ............ A61B 10/0038; A61B 2503/40; G06T 7/0014; G06T 2207/10056;
(Continued)

(56) References Cited

U.S. PATENT DOCUMENTS 9,933,425 B2 * 4/2018 Slusarewicz ..... G01N 33/56905
2012/0135457 A1 * 5/2012 Sowerby ................ G01N 21/03
435/288.7

(Continued)

FOREIGN PATENT DOCUMENTS

EP   3401665 A1   11/2018

OTHER PUBLICATIONS

International Search Report related to Application No. PCT/EP2019/084770; reported on Mar. 26, 2020.

(Continued)

*Primary Examiner* — Ming Y Hon
(74) *Attorney, Agent, or Firm* — von Briesen & Roper, s.c.

(57) ABSTRACT

A portable kit for generating a digital image of a faecal sample suitable for microscopic analysis, comprises a faecal sample preparation device configured to receive a faecal sample and a faecal flotation fluid, filter a suspension comprising the faecal sample and the faecal flotation fluid to provide a filtrate, a translucent faecal sample support, and a portable digital imaging module. The portable digital imaging module comprises a housing, a camera/microscopic lens assembly configured to generate a digital image of the faecal sample on the sample support, an illumination system, a seat for receiving the faecal sample support disposed between the camera/microscopic lens assembly and illumination system, a memory for storing the digital image, a communication system for communicating the digital image to an off-site image processing module via a communications network, (Continued)

and a battery operatively connected to the camera and microscopic lens assembly, memory and communication system.

33 Claims, 6 Drawing Sheets

(51) Int. Cl.

| | | |
|---|---|---|
| *B01L 3/00* | (2006.01) | |
| *G01N 1/31* | (2006.01) | |
| *G01N 1/38* | (2006.01) | |
| *G01N 1/40* | (2006.01) | |
| *G01N 33/50* | (2006.01) | |
| *G02B 21/36* | (2006.01) | |
| *G16H 30/20* | (2018.01) | |
| *H04N 23/50* | (2023.01) | |
| *H04N 23/56* | (2023.01) | |

(52) U.S. Cl.
CPC ............... *G01N 1/31* (2013.01); *G01N 1/38* (2013.01); *G01N 1/4077* (2013.01); *G02B 21/365* (2013.01); *G02B 21/368* (2013.01); *G06T 7/0014* (2013.01); *G16H 30/20* (2018.01); *H04N 23/50* (2023.01); *H04N 23/56* (2023.01); *A61B 2503/40* (2013.01); *B01L 2200/0652* (2013.01); *B01L 2200/18* (2013.01); *B01L 2300/023* (2013.01); *B01L 2300/024* (2013.01); *B01L 2300/027* (2013.01); *B01L 2300/043* (2013.01); *B01L 2300/046* (2013.01); *B01L 2300/0609* (2013.01); *B01L 2300/0654* (2013.01); *B01L 2300/0663* (2013.01); *B01L 2300/0681* (2013.01); *B01L 2300/126* (2013.01); *B01L 2300/168* (2013.01); *G01N 2001/4088* (2013.01); *G06T 2207/10056* (2013.01); *G06T 2207/20081* (2013.01)

(58) Field of Classification Search
CPC .......... G06T 2207/20081; G16H 30/20; H04N 23/50; H04N 23/56
See application file for complete search history.

(56) References Cited

U.S. PATENT DOCUMENTS

| | | | |
|---|---|---|---|
| 2016/0290916 A1 | 10/2016 | Ben Shoshan et al. | |
| 2017/0061608 A1* | 3/2017 | Kim | H04L 67/06 |
| 2018/0211380 A1 | 7/2018 | Tandon et al. | |
| 2018/0322660 A1* | 11/2018 | Smith | G06T 7/97 |
| 2019/0271632 A1* | 9/2019 | Yang | G01N 15/1434 |
| 2019/0289826 A1* | 9/2019 | Tippery | G06N 20/20 |
| 2020/0025686 A1* | 1/2020 | Chou | G01N 21/78 |
| 2020/0068286 A1* | 2/2020 | Schrems | H04R 1/1016 |
| 2020/0175611 A1* | 6/2020 | Gelfand | G06F 16/27 |
| 2020/0330029 A1* | 10/2020 | Chou | G01N 33/53 |

OTHER PUBLICATIONS

Jose C. Contreras-Naranjo, et al., "Mobile Phone-Based Microscopy, Sensing, and Diagnostics", IEEE Journal of Selected Topics in Quantum, Electronics, IEEE Service Center, Piscaway, NJ, US, vol. 22, No. 3, May 1, 2016, pp. 1-14, XP011587882, ISSN: 1077-260X, DOI: 10.1109/JSTQE.2015.2478657 [retrieved on Oct. 21, 2015] the whole document.

* cited by examiner

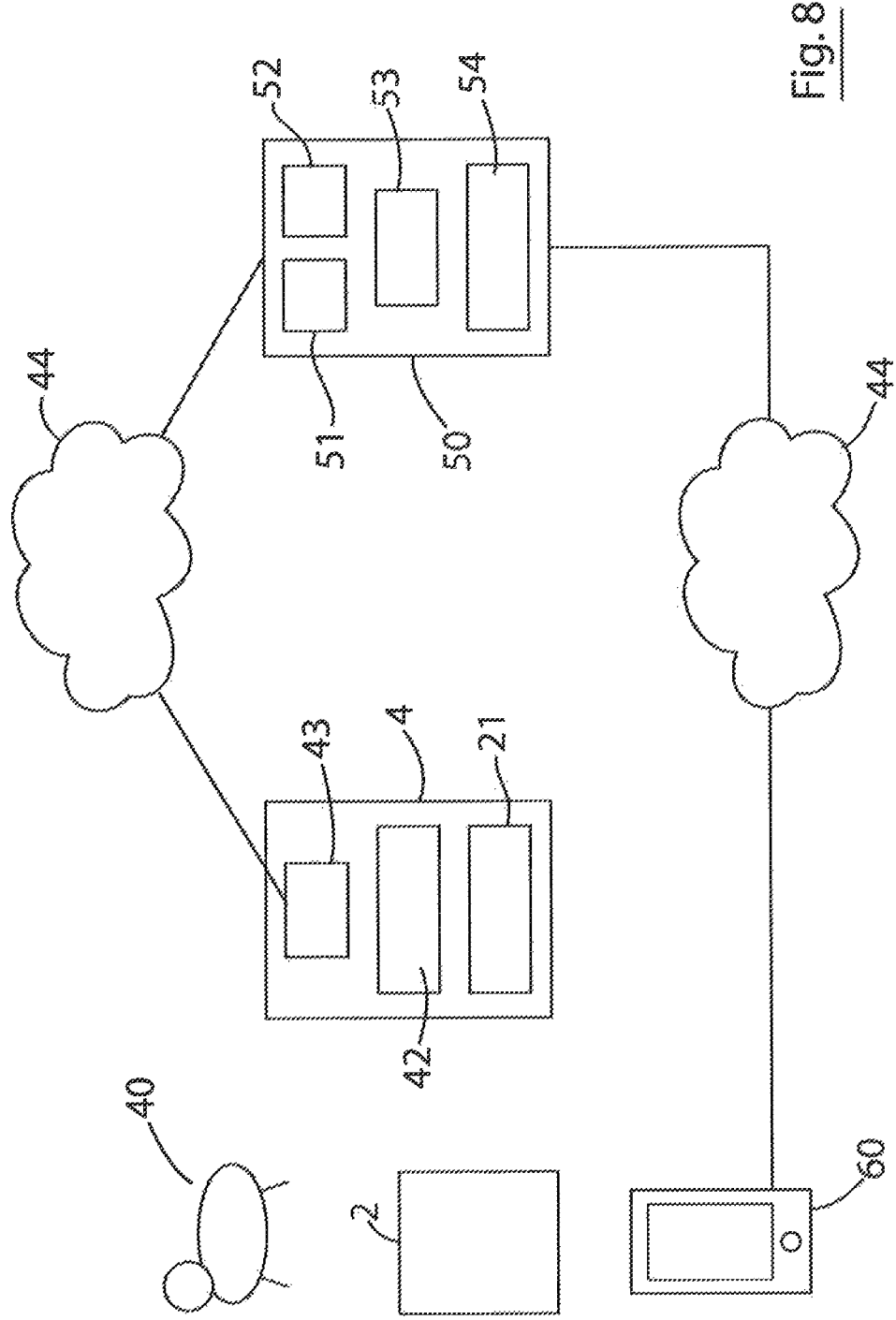

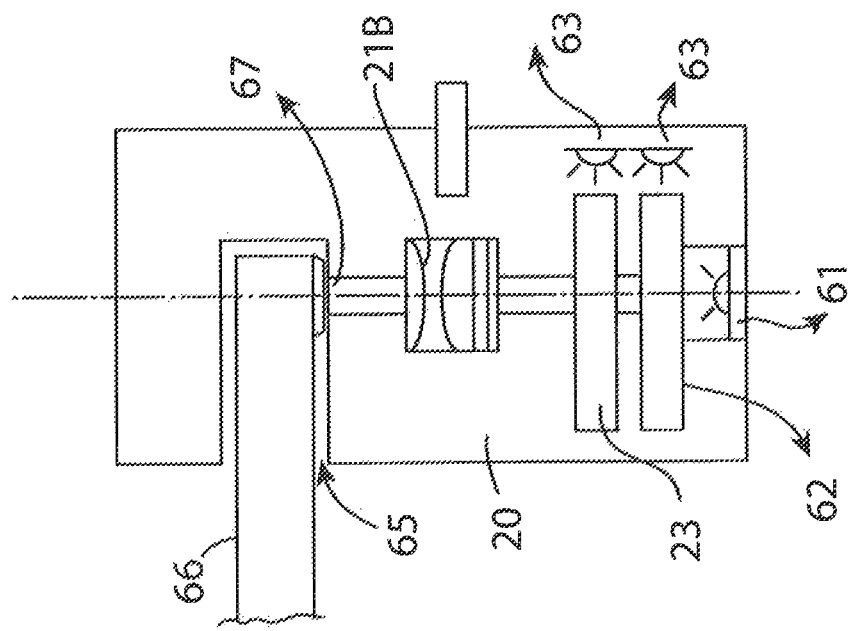
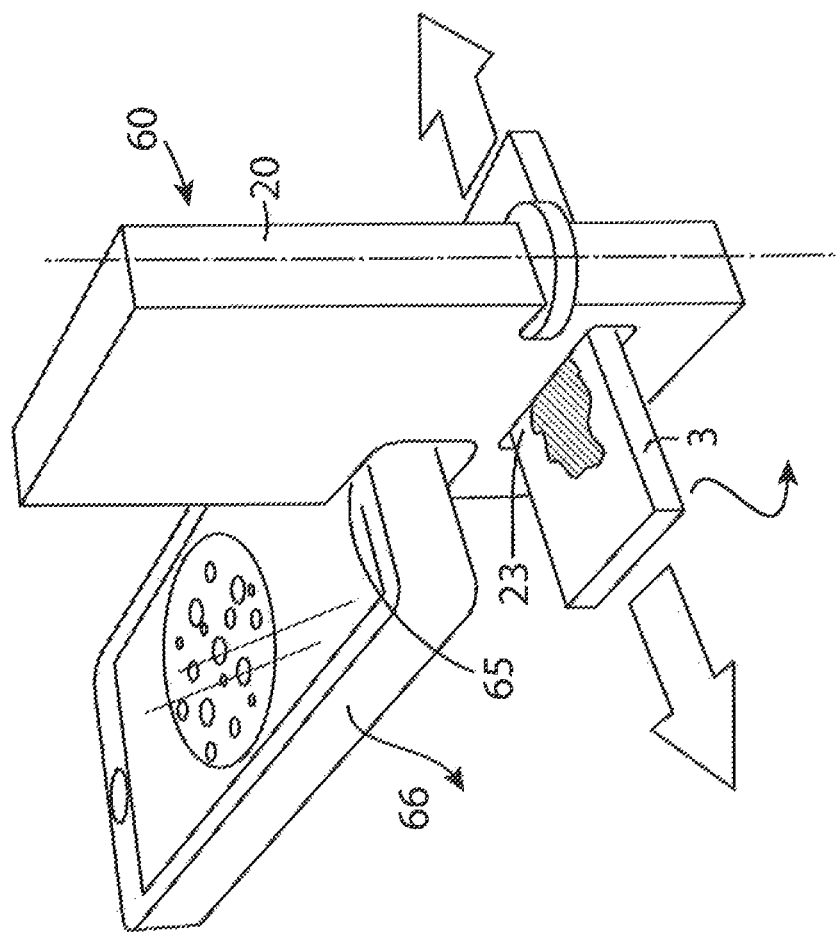
Fig. 9A
Fig. 9B

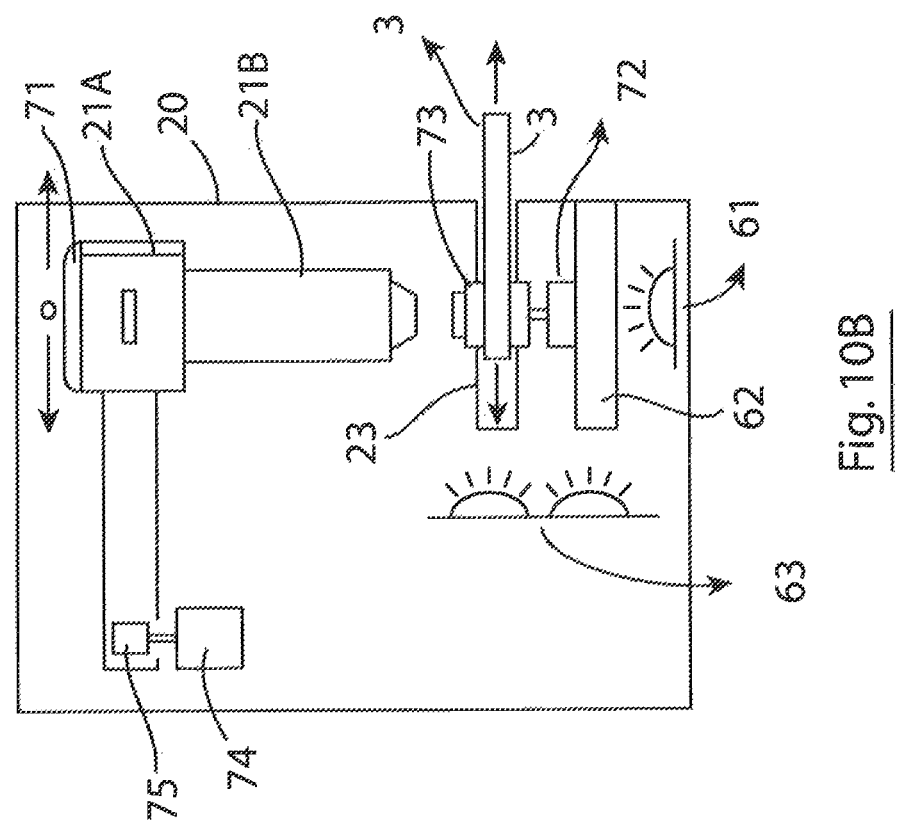
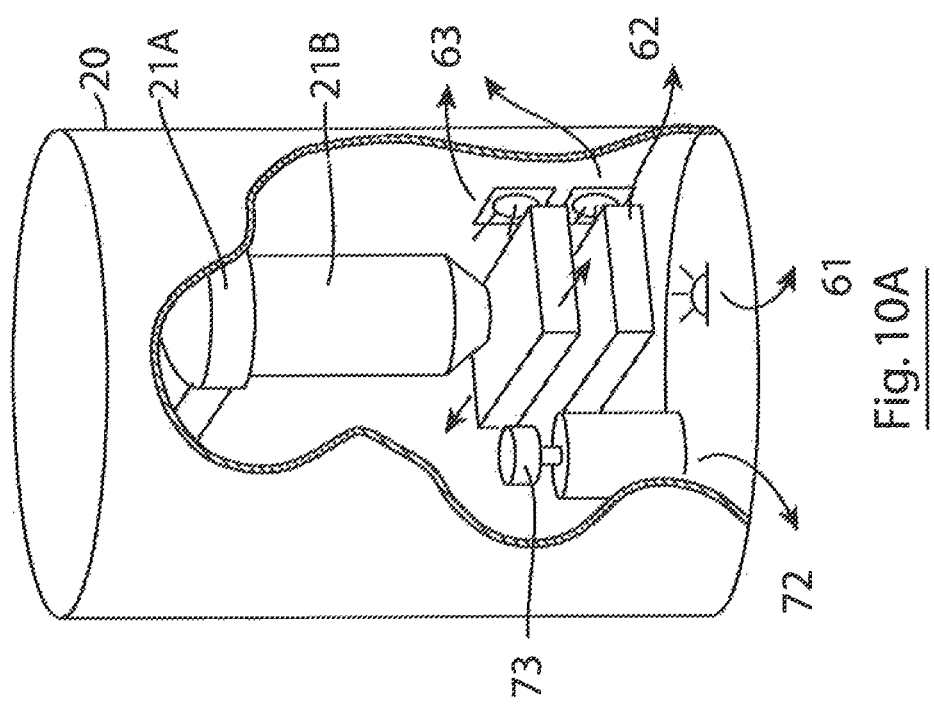

ON-SITE DETECTION OF PARASITIC INFECTION OF MAMMALS

CROSS-REFERENCE TO RELATED APPLICATIONS

This patent application is a 35 U.S.C. § 371 U.S. national stage filing of International Application No. PCT/EP2019/084770, filed in the European Patent Office as Receiving Office on Dec. 11, 2019, and claims priority to, and the benefit of, GB Patent Application No. 1820327.3, filed Dec. 13, 2018, the disclosures of which are hereby incorporated by reference in their entireties.

FIELD OF THE INVENTION

The present invention relates to a kit and method for on-site detection of a parasitic infection of a mammal, in particular infection with an internal parasite. Also contemplated are devices used in the kit and method.

BACKGROUND TO THE INVENTION

Parasitic diseases of cattle impair health, reproduction, growth, and productivity. In severe cases, parasitic diseases may even cause death. These diseases are caused by internal helminths (roundworms, tapeworms and flukes) as well as external arthropods (mites, lice, ticks, and flies). Transmission of helminths is through oral ingestion or direct skin penetration by larval parasites on pasture. Currently, internal parasitic infection is diagnosed in a laboratory by faecal analysis, using faecal egg or larval counts. This is a manual process where a faecal sample from the animal is transported to a laboratory, prepared and then visually analysed under magnification to determine an egg or larval count, from which infection can be determined qualitatively or quantitatively. Once infection is determined, the affected mammals can be treated with a suitable treatment product, for example avermectins and chloromectins for the control of worms or fluke.

Currently, many farmers prefer to dose their whole herd as opposed to testing their cattle for infection and only treating the cattle shown to be infected. This is at least partly due to the costs of testing, and the delays between testing and getting results. The practice of treating every animal in a herd results in a great over-usage of anti-parasite medication, which leads to drug resistance problems in the herd, cattle being treated with the wrong medication, and a resistance amongst farmers to adapt livestock management practices intended to reduce anti-parasitic resistance.

It is an object of the invention to overcome at least one of the above-referenced problems.

SUMMARY OF THE INVENTION

The present invention addresses the problem of over-use of anti-parasitic drugs by providing a system, kit and method for preparing a faecal sample suitable for digital imaging on-site, generating a digital image of the faecal sample on-site which is suitable for microbial analysis, and communicating the digital image to an off-site image analysis module via a wireless communications network suitable for use in a field or anywhere on a farm, and receipt of a parasitic infection characteristic for the mammal to a mobile communication device in near-real time (for example, within a few minutes). In this context, the term "on-site" refers to a place where mammals are kept, for example a farm, and off-site refers to a location that is remote to the farm, for example a laboratory. The kit, system and method of the invention allows a farmer rapidly prepare a sample and generate an image of the sample that is suitable for microbial analysis, which is automatically sent to a remote image analysis facility via wireless communication. The image can then be analysed by a processor to determine one or characteristics of the faecal sample. The analysis may employ image analysis recognition software to compare the image, or parts of the image, with reference images to correlate the test image with characteristics, for example detection of parasite eggs, identification of parasite eggs, quantification of parasitic infection. The characteristics of the sample may then be communicated back to the farmer, within minutes of the digital image of the faecal sample being taken. This allows a farmer then dose the mammal being tested almost immediately after the test has been performed.

The invention provides a system for on-site determination of a parasitic infection characteristic of a mammal, typically a non-human mammal, comprising
 a portable faecal sample preparation device (typically configured for use on-site to receive faecal matter from the mammal and a faecal flotation fluid, mix the faecal matter and faecal flotation fluid to provide a suspension, and filter the suspension to provide a filtrate, in which the filtrate is the faecal sample);
 a faecal sample support (that may be translucent);
 a portable digital imaging module adapted to generate a digital image of a faecal sample on the sample support and communicate the digital image via a wireless communications network;
 an off-site digital image analysis module configured to receive the digital image of the faecal sample via the wireless communication network, analyse the digital image to determine a parasitic infection characteristic of the sample, and communicate the parasitic infection characteristic of the sample via a wireless communications network; and
 software for a mobile communications device configured to cause the mobile communications device communicate with and receive the parasitic infection characteristic of the sample, from the of-site digital image processing module via a wireless communication network.

Optionally, in any embodiment, the portable digital imaging module is configured to communicate the digital image to the off-site digital image analysis module via the mobile communications device.

Optionally, in any embodiment, the portable digital imaging module comprises a communication module to communicate the digital image to the off-site digital image analysis module via the wireless communications network.

Optionally, in any embodiment, the software for the mobile communications device is configured to cause the mobile communications device to:
 receive the digital image of the faecal sample;
 communicate the digital image to the off-site digital image analysis module; receive the parasitic infection characteristic of the sample from the off-site digital image analysis module; and
 display the parasitic infection characteristic of the sample on the screen of the mobile communications device.

Optionally, in any embodiment, the software for the mobile communications device is configured to cause the mobile communications device to:

request input of identification data for the mammal into the mobile communications device;

receive and store identification data for the mammal;

display on the screen of the mobile communications device the parasitic infection characteristic of the sample and the mammal identification data.

Optionally, in any embodiment, the software for the mobile communications device is configured to cause the mobile communications device to store parasitic infection characteristics of the sample for the same mammal obtained over a period of time, and display the parasitic infection characteristics.

Optionally, in any embodiment, the software is a downloadable mobile device software application (i.e. a mobile device "app").

Optionally, in any embodiment, the portable digital imaging module comprises:

a camera and lens assembly configured to generate the digital image of the sample on the sample support;

a sample support illumination system;

a seat for receiving the sample support; and a battery operatively connected to the camera and lens assembly, memory and illumination system.

Optionally, in any embodiment, the lens is 4× to 12× lens.

Optionally, in any embodiment, the camera of the camera and lens assembly is provided by a camera of the mobile communications device, in which the portable digital imaging module is configured for detachable engagement with the mobile communications device in a sample support imaging position.

Optionally, in any embodiment, the portable digital imaging module is configured for snap-fit attachment to the mobile communications device.

Optionally, in any embodiment, the portable digital imaging module is adapted to provide relative movement between the sample support and the camera and lens assembly to allow generation of a plurality of digital images across the sample support Optionally, in any embodiment, the portable digital imaging module comprises a seat adjustment module configured for lateral adjustment of the seat relative to the camera and lens assembly upon actuation, or a camera and lens adjustment module configured for lateral adjustment of the camera and lens assembly relative to the seat upon actuation, or both.

Optionally, in any embodiment, the seat adjustment module and/or camera and lens adjustment module are configured for manual adjustment.

Optionally, in any embodiment, the portable digital imaging module comprises an actuating motor operatively connected to the seat adjustment module and/or camera and lens adjustment module.

Optionally, in any embodiment, the lens is an ultra-wide angle lens.

Optionally, in any embodiment, the camera is configured to generate an ultra-high resolution image. This allows digital im Optionally, in any embodiment, the seat for the sample support is disposed between the sample support illumination system ad camera and lens assembly.

Optionally, in any embodiment, the illumination system comprises a direct light source disposed under the seat for the sample support, and an indirect light source disposed at one side of the seat for the sample support.

Optionally, in any embodiment, the faecal sample support (slide) is a McMaster slide. Other sample supports such as glass slides may be employed.

Optionally, in any embodiment, the portable faecal sample preparation device comprises a vessel with an opening and a detachable closure for the opening of the vessel, wherein the closure detachable comprises an openable lid and a filter disposed between the opening of the vessel and the closable lid.

Optionally, in any embodiment, the portable faecal sample preparation device additionally comprises low-cost paper centrifugation device configured to centrifuge the filtrate.

Optionally, in any embodiment, the off-site image processing module comprises a processor to analyse the digital image by correlating the digital image or a part of the digital image with a characteristic of the faecal sample by comparing the digital image or the part of the digital image with one or more, ideally a database, of references images or features from the reference images.

Optionally, in any embodiment, the processor is configured to analyse the digital image by deep learning.

Optionally, in any embodiment, the processor comprises a computational model configured to:

receive an input comprising the digital image or features extracted from the digital image, in which the computational model is generated from a training set of digital images of faecal samples of known parasitic infection characteristics; and output a characteristic of the faecal sample selected from diagnosis of parasitic infection, type of parasitic infection, extent or stage of infection.

The invention also provides a method of on-site detection of a parasitic infection of a mammal, comprising the steps of:

preparing on-site a faecal sample for imaging, typically by mixing the faecal sample with a faecal flotation fluid and filtering the faecal flotation fluid through a filter to provide a filtrate, in which the filtrate is the faecal sample;

placing a drop of the faecal sample on or in a translucent sample support;

generating, onsite, using a portable digital imaging module comprising a communication system adapted to communicate the digital image to an off-site image processing module via a wireless communications network, a digital image of the faecal sample on the sample support;

communicating the digital image, using the communication system, to an off-site digital image analysis module via a wireless communication network;

analysing, off-site by the digital image analysis module, the digital image to determine a parasitic infection characteristic of a sample; and communicate the parasitic infection characteristic of the sample via a wireless communications network to an on-site mobile communications device comprising software configured to communicate with, and receive the parasitic infection characteristic of the sample, from the off-site digital image processing module via the wireless communication network.

Optionally, in any embodiment, the digital image is communicated to the off-site digital image analysis module by the on-site mobile communications device.

Optionally, in any embodiment, the digital image is communicated to the off-site digital image analysis module by a communications module forming part of the portable digital imaging module.

Optionally, in any embodiment, the method of the invention includes the steps of:

receiving by the mobile communications device a digital image of the faecal sample;

communicating by the mobile communications device the digital image to the off-site digital image analysis module;

receiving by the mobile communications device the parasitic infection characteristic of the sample from the off-site digital image analysis module; and displaying by the mobile communications device the parasitic infection characteristic of the sample on the screen of the mobile communications device.

Optionally, in any embodiment, the method of the invention includes the steps of:

requesting by the mobile communications device input of identification data for the mammal into the mobile communications device;

receiving and storing by the mobile communications device identification data for the mammal;

displaying by the mobile communications device the parasitic infection characteristic of the sample and the mammal identification data.

Optionally, in any embodiment, the method of the invention includes the step of storing by the mobile communications device parasitic infection characteristics of the sample for the same mammal obtained over a period of time, and displaying by the mobile communications device the parasitic infection characteristics over time.

Optionally, in any embodiment, the digital image of the faecal sample on the sample support is generated by a camera of the mobile communications device, in which the portable digital imaging module is configured for detachable engagement with the mobile communications device in a sample support imaging position.

Optionally, in any embodiment, the portable digital imaging module is adapted to provide relative movement between the sample support and the camera and lens assembly, in which the method includes generation of a plurality of digital images while moving the sample support relative to the camera and lens assembly to generate of a plurality of digital images across the sample support.

Optionally, in any embodiment, the method includes a step of illuminating an underside of the sample support with direct light and a side of the sample support with indirect light during the generation of the digital image of the sample support.

Optionally, in any embodiment, the step of analysing, off-site by the digital image analysis module, the digital image to determine a parasitic infection characteristic of a sample comprises comparing the digital image or the part of the digital image with one or more, ideally a database, of references images or features from the reference images to correlating the digital image or a part of the digital image with a characteristic of the faecal sample.

Optionally, in any embodiment, the digital image is analysed by deep learning.

Optionally, in any embodiment, the step of preparing on-site a faecal sample additionally includes a step of centrifugation of the filtrate from the filtration step, in which a pellet obtained by centrifugation is resuspended in a suitable solution (i.e. salt/zinc) to provide the faecal sample.

The invention also provides a mobile kit suitable for use off-site comprising:

a portable faecal sample preparation device configured for use on-site (typically to receive faecal matter from the mammal and a faecal flotation fluid, mix the faecal matter and faecal flotation fluid to provide a suspension, and filter the suspension to provide a filtrate, in which the filtrate is the faecal sample);

a faecal sample support;

a portable digital imaging module adapted to generate a digital image of a faecal sample on the sample support and communicate the digital image via a wireless communications network to an off-site digital image processing module via a wireless communication network for off-site analysis of the digital image to determine a parasitic infection characteristic of a sample; and software for a mobile communications device configured to cause the mobile communications device communicate with, and receive the parasitic infection characteristic of the sample, from the of-site digital image processing module via a wireless communication network.

Optionally, in any embodiment, the portable digital imaging module comprises:

a camera and lens assembly configured to generate the digital image of the sample on the sample support;

a sample support illumination system;

a seat for receiving the sample support; and a battery operatively connected to the camera and lens assembly, memory and illumination system.

Optionally, in any embodiment, the camera of the camera and lens assembly is provided by a camera of the mobile communications device, in which the portable digital imaging module is configured for detachable engagement with the mobile communications device in a sample support imaging position.

Optionally, in any embodiment, the portable digital imaging module is configured for snap-fit attachment to the mobile communications device.

Optionally, in any embodiment, the portable digital imaging module is adapted to provide relative movement between the sample support and the camera and lens assembly to allow generation of a plurality of digital images across the sample support Optionally, in any embodiment, the portable digital imaging module comprises a seat adjustment module configured for lateral adjustment of the seat relative to the camera and lens assembly upon actuation, or a camera and lens adjustment module configured for lateral adjustment of the camera and lens assembly relative to the seat upon actuation, or both.

Optionally, in any embodiment, the seat adjustment module and/or camera and lens adjustment module are configured for manual adjustment.

Optionally, in any embodiment, the portable digital imaging module includes an actuating motor operatively connected to the seat adjustment module and/or camera and lens adjustment module.

Optionally, in any embodiment, the lens is an ultra wide angle lens.

Optionally, in any embodiment, the camera is configured to generate an ultra high resolution image.

Optionally, in any embodiment, the seat for the sample support is disposed between the sample support illumination system ad camera and lens assembly.

Optionally, in any embodiment, the illumination system comprises a direct light source disposed under the seat for the sample support, and an indirect light source disposed at one side of the seat for the sample support.

Optionally, in any embodiment, the faecal sample support is a McMaster slide.

The invention also provides a portable digital imaging module comprising a housing having:
- a seat for receiving a sample support slide;
- a lens for imaging a sample support received on the seat;
- a sample support slide illumination system; and
- a battery operatively connected to the illumination system,
- wherein the housing is configured for detachable engagement with a mobile communications device to form a portable digital imaging assembly in which a camera of the mobile communications device and the lens of the portable digital imaging module forms a camera and lens assembly configured to generate a digital image of a sample support slide on the seat.

Optionally, in any embodiment, the portable digital imaging module is configured for snap-fit attachment to the mobile communications device.

Optionally, in any embodiment, the portable digital imaging module is adapted to provide relative movement between the sample support and the camera and lens assembly to allow generation of a plurality of digital images across the sample support Optionally, in any embodiment, the portable digital imaging module comprises a seat adjustment module configured for lateral adjustment of the seat relative to the camera and lens assembly upon actuation, or a camera and lens adjustment module configured for lateral adjustment of the camera and lens assembly relative to the seat upon actuation, or both.

Optionally, in any embodiment, the seat adjustment module and/or camera and lens adjustment module are configured for manual adjustment.

Optionally, in any embodiment, the portable digital imaging module includes an actuating motor operatively connected to the seat adjustment module and/or camera and lens adjustment module.

Optionally, in any embodiment, the portable digital imaging module the lens is an ultra-wide angle lens.

Optionally, in any embodiment, the portable digital imaging module the camera is configured to generate an ultra-high resolution image.

Optionally, in any embodiment, the portable digital imaging module the seat for the sample support is disposed between the sample support illumination system ad camera and lens assembly.

Optionally, in any embodiment, the portable digital imaging module the illumination system comprises a direct light source disposed under the seat for the sample support, and an indirect light source disposed at one side of the seat for the sample support.

Optionally, in any embodiment, the portable digital imaging module the sample support slide is a McMaster slide.

The invention also provides a portable faecal sample preparation device configured to receive faecal matter and a faecal flotation fluid, mix the faecal matter and faecal flotation fluid to provide a suspension, and filter the suspension to provide a filtrate, in which the filtrate is the faecal sample), the device comprising a vessel with an opening and a detachable closure for the opening of the vessel, wherein the closure detachable comprises an openable lid and a filter disposed between the opening of the vessel and the closable lid. The device is used by removing the detachable closure from the opening of the vessel, placing some faecal matter in the vessel, adding some liquid reagent (i.e. flotation fluid), re-attaching the closure, shaking the device to provide a liquid suspension in the vessel, then opening the lid at the top of the closure while the closure is attached to the vessel, and inverting the vessel so that liquid in the vessel is filtered through the filter and exits through the open lid.

The detachable closure is configured for screw attachment to the top of the vessel. The lid is generally a hinged lid, typically configured for snap-fit closure. The filter is configured to span the width of the lid. The device is generally a single-use device, and formed from polymer.

According to another aspect of the present invention, there is provided a portable kit to generate a digital image of a faecal sample suitable for microscopic analysis, comprising:
- a faecal sample preparation device (typically configured to receive faecal matter and a faecal flotation fluid, mix the faecal matter and faecal flotation fluid to provide a suspension, and filter the suspension to provide a filtrate, in which the filtrate is the faecal sample);
- a translucent faecal sample support; and
- a portable digital imaging module comprising a communication system and adapted to generate a digital image of a faecal sample on the sample support; and
- communicate the digital image to an off-site image processing module via a communications network.

In one embodiment, the digital imaging module comprises a housing containing:
- a camera and microscopic lens assembly configured to generate a digital image of the sample on the sample support;
- optionally, an illumination system;
- a seat for receiving the sample support disposed between the camera and microscopic lens assembly and illumination system;
- a memory for storing the digital image;
- a communication system for communicating the digital image to an off-site image processing module via a communications network; and
- optionally, a battery operatively connected to the camera and microscopic lens assembly, memory and communication system.

In any embodiment, the sample preparation device comprises a vessel with an opening and a closure fitting to close the opening of the vessel, wherein the closure fitting comprises an openable lid and a filter disposed between the opening of the vessel and the closable lid.

In any embodiment, the camera comprises a CCD or CMOS sensor.

In any embodiment, the sample support is a glass slide, optionally with a translucent cover-slip.

In any embodiment, the kit includes a plurality of sample supports and a plurality of sample preparation devices.

In any embodiment, the kit includes a plurality of faecal matter sampling spoons.

In any embodiment, the faecal flotation fluid is a flotation fluid such as for example a saturated salt solution or sugar/salt solution. In one embodiment, the solution has a solute concentration of 20-50%, In any embodiment, the seat for receiving the sample support is horizontally adjustable between an extended position proud of the housing to a retracted position within the housing.

In another aspect, the invention provides a system comprising a portable kit according to the invention, in combination with an off-site digital image analysis module configured to receive the digital image of the prepared sample via a communication network and analyse the digital image to determine a characteristic of a sample.

In one embodiment, the off-site image processing module comprises a processor to analyse the image by correlating the image (or a part of the image) with a characteristic of the faecal sample by comparing the image (or the part of the image) with one or more, ideally a database, of references images (or features from the reference images). Diagnosis of intestinal parasites by artificial intelligence/deep learning techniques are described in the literature, for example in the following publications:

(https://www.researchgate.net/profile/Alan_Peixinho/publication/309203871_Diagnosis_of_Human_Intestinal-_Parasites_by_Deep_Learning/links/580519be08aee314f68e2057/Diagn osis-of-Human-Intestinal-Parasites-by-Deep-Learning.pdf?origin=publication_detail), http://www.biomedres.info/biomedical-research/classification-of-parasite-egg-cells-using-gray-level-cooccurence-matrix-and-knn.html https://arxiv.org/pdf/1608.02989.pdf In any embodiment of the kit, system and methods of the invention, the processor comprises a computational model configured to:

receive an input comprising the digital image or features extracted from the digital image, in which the computational model is generated from a training set of digital images of faecal samples of known characteristics (i.e. known parasitic infection status); and output a characteristic of the faecal sample (for example a characteristic selected diagnosis of parasitic infection, type of parasitic infection, extent or stage of infection).

In any embodiment, the off-site image processing module comprises a processor to analyse the image by:

acquiring the digital image;

extracting spectral features from the digital image;

comparing the spectral features with a plurality of images in a training set to determine a characteristic of the sample.

In any embodiment, the processor is configured to determine a parasitic infection characteristic of the sample selected from:

the presence of parasitic infection;

the type of parasitic infection; and the severity of the parasitic infection.

In any embodiment, the off-site image processing module comprises a communication module configured to communicate data, for example a determined characteristic of the faecal sample (diagnosis of parasitic infection, type or extent of infection, suitable treatment for the infection), to a remote computing device via a communication network. This may be a computer, or a mobile device such as a tablet or mobile phone. The computing device may comprise software configured to communicate with, and receive date from, the image processing module. The software may be a downloadable mobile phone application. In one embodiment, the kit and system of the invention comprise a downloadable mobile phone application software configured to communicate with, and receive date from, the image processing module. The data may include information relating to the presence or absence of infection, the type of infection (i.e. fluke or roundworm), the stage of infection, prognostic information, and information relating to a suitable treatment for the animal.

In another aspect, the invention provides a method for generating a digital image of a faecal sample suitable for microscopic analysis, comprising the steps of:

preparing on-site a faecal sample for imaging by mixing the faecal sample with a faecal flotation fluid and filtering the faecal flotation fluid through a filter to provide a filtrate, in which the filtrate is the faecal sample;

placing a drop of the faecal sample on a translucent sample support;

generating, on-site, using a portable digital imaging module comprising a communication system adapted to communicate the digital image to an off-site image processing module via a communications network, a digital image of a prepared sample on the sample support; and communicating the digital image, using the communication system, to an off-site digital image analysis module via a communication network.

In any embodiment, the method includes the step of analysing, off-site by the image processing module, the digital image to determine a characteristic of a sample.

In any embodiment, the method includes the steps of:

acquiring, by the processor, the digital image;

extracting, by the processor, spectral features from the digital image; and comparing, by the processor, the spectral features with a plurality of images in a training set to determine a characteristic of the sample.

In any embodiment, the method includes the step of determining, by the processor, a parasitic infection characteristic of the sample typically selected from:

the presence of parasitic infection;

the type of parasitic infection; and the severity of the parasitic infection.

In any embodiment, the digital imaging module comprises a housing containing:

a camera and microscopic lens assembly configured to generate a digital image of the sample on the sample support;

an illumination system;

a seat for receiving the sample support disposed between the camera and microscopic lens assembly and illumination system;

a memory for storing the digital image;

a communication system for communicating the digital image to an off-site image processing module via a communications network; and a battery operatively connected to the camera and microscopic lens assembly, memory and communication system.

In another aspect, the invention provides a method of treating a mammal for a parasitic infection, comprising the steps of:

determining the presence of a parasitic infection in the mammal using a method according to the invention; and treating the mammal determined to have a parasitic infection with a suitable medicament.

In another aspect, the invention provides a portable digital imaging module comprises a housing containing:

a camera and microscopic lens assembly configured to generate a digital image of the sample on the sample support;

optionally, an illumination system;

a seat for receiving the sample support (i.e. a glass slide) disposed between the camera and microscopic lens assembly and illumination system;

a memory for storing the digital image;

a communication system for communicating the digital image to an off-site image processing module via a communications network; and optionally, a battery operatively connected to the camera and microscopic lens assembly, memory and communication system.

There is also provided a computer program comprising program instructions for causing a computer program to carry out at least one step of a method of the invention which may be embodied on a record medium, carrier signal or read-only memory.

In any embodiment herein, the portable faecal sample preparation device may employ other means for separating eggs from other faecal matter, for example a portable centrifugation device that may be used on-site, optionally in combination with a filtration apparatus.

The kit, device, system and method of the invention is described with use for analysis of faecal samples, however it will be appreciated that they may be employed for analysis and other biological samples, for example urine, blood, and blood products, and for use with humans and other non-human mammals.

Other aspects and preferred embodiments of the invention are defined and described in the other claims set out below.

BRIEF DESCRIPTION OF THE FIGURES

FIG. 5 is an illustration of the steps of the invention;

FIG. 6 is an illustration of one of the steps of the method of the invention;

FIG. 7 is an illustration of one of the steps of the method of the invention;

FIG. 8 is a block diagram of a system for determining a characteristic of a faecal sample according to the invention.

FIGS. 9A and 9B are perspective, and sectional plan, views of a digital imaging module according to the invention.

FIGS. 10A and 10B are perspective, and sectional plan, views of a digital imaging module according to the invention.

DETAILED DESCRIPTION OF THE INVENTION

Figure 1:
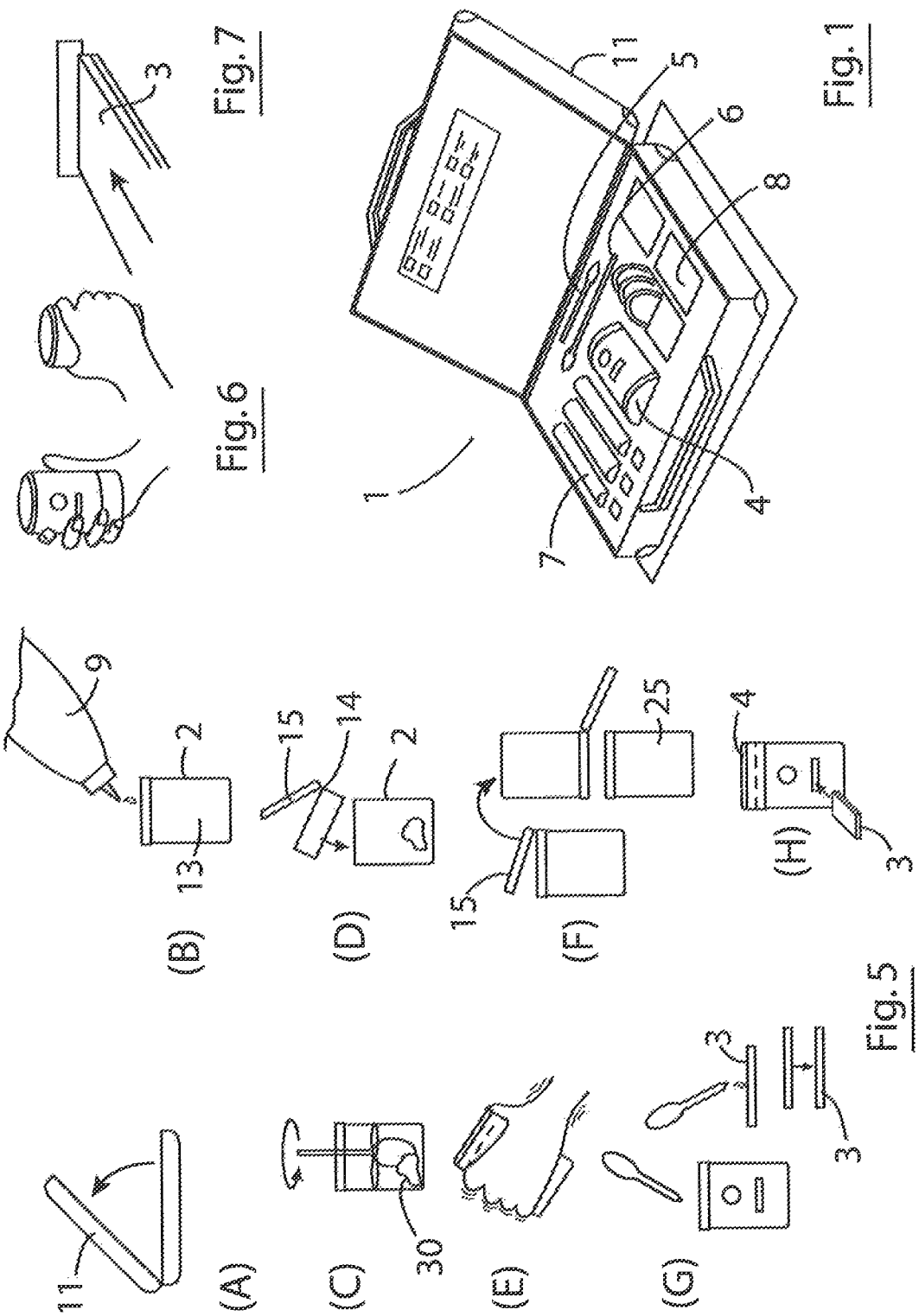
FIG. 1 is an illustration of a kit of the invention.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "on-site" refers to a place where mammals are kept, for example a farm or zoo, or in the wild. For domestic animals, this would refer to a home or kennels or a veterinarian clinic. As used herein, the term "off-site" refers to a place remote to the on-site, for example a laboratory or office.

As used herein, the term "parasitic infection characteristic" as applied to the sample refers to a characteristic of the sample which provides information relating to parasitic infection status of the mammal/For example, the characteristic could be any one or more of the following: presence of parasite eggs or larvae; identity of the eggs or larvae; quantification of eggs or larvae (absolute or relative); and stage of infection.

As used herein, the term "faecal sample preparation device" refers to a device that is portable and can be used on-site and treats a faecal sample to remove coarse matter from the sample leaving microscopic matter such as parasite eggs and larvae. This may be achieved by filtration and/or centrifugation. Examples of low-cost paper centrifuges are described in Nature Biomedical Engineering (Jan. 10, 2017).

As used herein, the term "flotation fluid" refers to fluid that is used to separate parasitic eggs and oocysts from faecal matter and float the eggs/oocysts to the top of the fluid. The fluids are configured to be more dense that parasite eggs/oocysts, and therefore generally comprise a concentrated salt or sugar solution. The fluid is generally mixed with faecal matter and then filtered to provide a filtrate which will contain the eggs and oocysts if an infection is present. Flotation fluids for parasitic diagnosis are described in: https://www.rvc.ac.uk/review/parasitology/Flotation/Flotation_fluids/General.htm https://vetlabsupplies.co.uk/products/laboratoy-consumabes/flotation-solutions/http://www.brunelmicroscopes.co.uk/flotation-fluid.html As used herein, the term "digital image analysis module" refers to a computation system configured to receive the digital image of the prepared sample via a communication network and analyse the digital image with a computational device comprising a processor to determine a characteristic of a sample. In one embodiment, the processor analyses the image by correlating the image (or a part of the image) with a characteristic of the faecal sample by comparing the image (or the part of the image) with one or more, ideally a database, of references images (or features from the reference images). Diagnosis of intestinal parasites by artificial intelligence/deep learning techniques are described in the literature, for example in the following publications:

(https://www.researchgate.net/profile/Alan_Peixinho/publication/309203871_Diagnosis_of_Human_Intestinal-_Parasites_by_Deep_Learning/links/580519be08aee314f68e2057/diagn osis-of-Human-intestinal-Parasites-by-Deep-Learning.pdf?origin=publication_detail), http://www.biomedres.info/biomedical-research/classification-of-parasite-egg-cells-using-gray-level-cooccurence-matrix-and-knn.html http://arxiv.org/pdf/1608.02989.pdf In one embodiment, the processor comprises a computational model configured to: receive an input comprising the digital image or features extracted from the digital image, in which the computational model is generated from a training set of digital images of faecal samples of known characteristics (i.e. known parasitic infection status); and output a characteristic of the faecal sample (for example a characteristic selected diagnosis of parasitic infection, type of parasitic infection, extent or stage of infection).

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Figure 2:
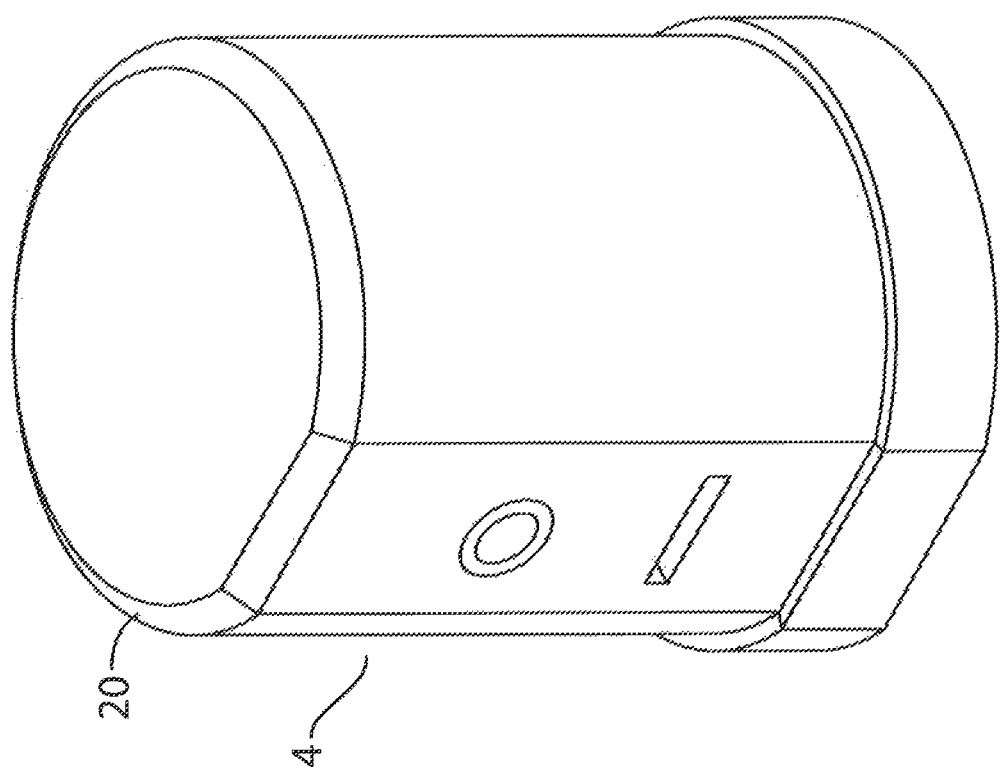
FIG. 2 is an image of a digital imaging module according to the invention.
Figure 3:
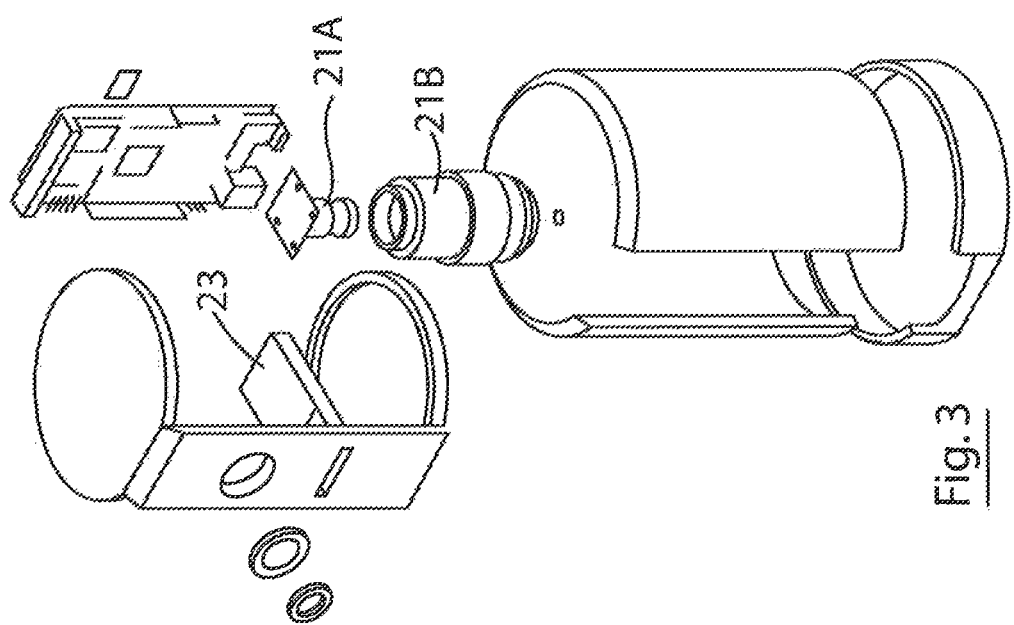
FIG. 3 is an exploded view of the components of the digital imaging module of FIG. 5.

Referring to the drawings, and initially to FIGS. 1 to 3, there is illustrated a portable kit for generating a digital image of a faecal sample suitable for microscopic analysis according to the invention, and indicated generally by the reference numeral 1. The kit comprises a faecal sample preparation device 2 configured to receive a faecal sample and a faecal flotation fluid, filter a suspension comprising the faecal sample and the faecal flotation fluid to provide a filtrate, a translucent sample support, in this example a glass slide 3, and a digital imaging module 4 configured to generate a digital image of the faecal sample and communicate the digital image to an off-site image analysis module. The kit also includes a spoon 5, dropper 6, filters 7, gloves 8, faecal flotation fluid 9, and instructions for use 10. All components of the kit are contained within a portable case 11.

Figure 4A:
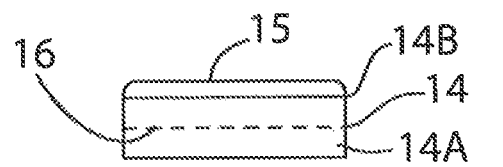
FIG. 4A is a perspective view of a faecal sample preparation device according to the invention shown with the closure separated from the vessel.
Figure 4B:
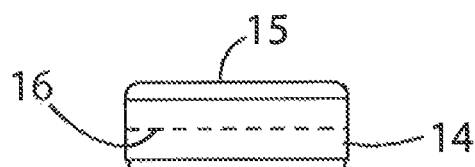
FIG. 4B is a perspective view of a faecal sample preparation device according to the invention shown with the closure attached to the vessel and the lid closed.
Figure 4C:
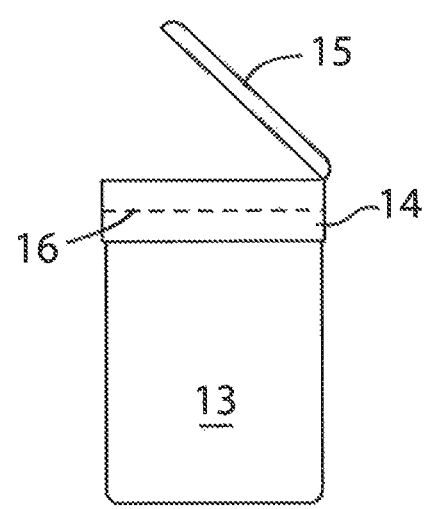
FIG. 4C is a perspective view of a faecal sample preparation device according to the invention shown with the closure attached to the vessel and the lid opened.

In more detail, and referring to FIGS. 4A to 4A, the faecal sample preparation device 2 comprises a vessel 13, and closure 14 configured for screw attachment to the mouth of the vessel. The closure comprises a first end 14A adapted for screw engagement with the mouth of the vessel, and second end 14B having an openable hinged lid 15, and a filter 16 disposed between the first and second ends. The filter is adapted to filter a suspension comprising the faecal matter and faecal flotation fluid 9 to provide a filtrate containing microscopic matter, such as parasite eggs or larvae.

In more detail, and referring to FIGS. 2 and 3, the portable digital imaging module 4 comprises a housing 20 containing a CCD camera 21A and microscopic lens assembly 21B configured to generate a digital image of the sample on the sample support, an illumination system, and a seat 23 for receiving the glass slide 3 disposed between the camera and microscopic lens assembly and illumination system. In this embodiment, the seat for the glass slide comprises a frame for supporting the slide along its periphery to allow light from the illumination system below the seat illuminate the underside of the slide 3. The seat 23 is configured for horizontal movement from an extended position prior of the housing to allow the slide be positioned on the seat, to a retracted, imaging, position within the housing. The module 4 also includes a memory for storing the digital image, a communication system for communicating the digital image to an off-site image processing module via a communications network, and a battery operatively connected to the camera and microscopic lens assembly, memory and communication system.

In use, and referring to FIGS. 5 to 7:

(A) The case 10 is opened and the components of the kit are removed for use.

(B) A volume of the flotation fluid 9 is then added to the vessel 13

(C) A sample of faecal matter 30, in this case faecal matter from a dairy cow, is added to the vessel. Typically 3-5 g of faecal matter is added to 50 mls of flotation fluid.

(D) The closure 14 is then screwed onto the mouth of the vessel closing the vessel.

(E) The vessel is then shaken manually to thoroughly mix the faecal matter and faecal flotation fluid and provide a suspension (FIG. 6).

(F) The lid 15 is then opened, and the vessel inverted to filter the suspension through the filter with the filtrate passing into a collection vessel 25

(G) A pipette is then used to withdraw some of the filtrate from the collection vessel and put a drop onto the glass slide 3 and a cover slip is placed on top.

(H) The glass slide is then placed into the digital imaging module (FIG. 7).

In another embodiment, the faecal sample preparation employs the above steps to produce a filtrate, and then the filtrate is centrifuged using a lost-cost portable paper centrifuge. The following steps may be employed:

(I) Some of the filtrate is withdrawn into a microfuge tube;

(J) the microfuge tube is attached radially to a paper disc of a paper centrifuge and centrifuged for three minutes (K) the supernatant is removed from the microfuge tube and the pellet is re-suspended in a salt/zinc solution by mixing (L) aliquots of the resultant suspension is pipetted into slots in a McMaster slide FIG. 8 shows a block diagram of a system for generating a digital image of a faecal sample, and determining a characteristic of the faecal sample according to an embodiment of the invention. The system may include a faecal sample preparation device 2 for preparing faecal sample from an animal 40, and a digital imaging module 4. The digital imaging module 4 may include a CCD camera 21A and lens assembly 21B, memory 42 and a communication device 43 for communicating digital image data to a remote site via a communication network 44. The CCD camera may collect information incident on the camera as a set of images which may be combined together to provide a 3-dimensional data cube for processing and analysis. The communication network 44 can be the internet, an intranet, or any wired or wireless communication network. For example, the communication network 44 may include a Mobile Communications (GSM) network, a code division multiple access (CDMA) network, 3$^{rd}$ Generation Partnership Project (GPP), an Internet Protocol (IP) network, a wireless application protocol (WAP) network, a WiFi network, or an IEEE 802.11 standards network, as well as various communications thereof. Other conventional and/or later developed wired and wireless networks may also be used. The digital imaging module may contain a processor for performing processing of the digital image captured by the device, or for synchronizing the operation of the digital imaging module including the taking, storage and communication of the digital image.

Although not illustrated, it will be appreciated that the digital imaging module 4 may be configured for electronic coupling to a mobile communications device (i.e. a mobile phone) by means of wired or wireless communication, where the digital image generated by the imaging module may be transmitted off-site by the mobile communications device.

The system may include an off-site digital image analysis module 50 configured to receive the digital image of the prepared sample via a communication network 44 and analyse the digital image to determine a characteristic of a sample. The module 50 may include an image processing application 53 that processes and analyzes each digital image captured by the imaging device 4. The module 50 may include and/or be in communication with a database 54 that may store data and images. In one example, the database 64 may store information such as a training set of data that may comprise a plurality of images of faecal samples. The plurality of images may be generated synthetically by the module and/or obtained from another source. In addition, the plurality of images may be captured by the imaging module 4 and included as part of the training set of data. Additionally, the database may store characteristics of the object in each of the plurality of images. These characteristics may include a label or name for the object and other information such as measurements of the object. The measurements may be assigned manually by users of the module 50 and/or determined automatically by the module 50 during analysis of the image. Additionally, the image processing application 53 may communicate with other computing devices via a communication network 44.

The image analysis module 50 includes at least one processor 51 to process data and memory 52 to store data. The processor 51 may process communications, build communications, retrieve data from memory 52, and store data to memory 52. The processor 51 and the memory 52 are hardware. The memory 52 may include volatile and/or non-volatile memory, e.g., a computer-readable storage medium such as a cache, random access memory (RAM), read only memory (ROM), flash memory, or other memory to store data and/or computer-readable executable instructions such as a portion or component of the image processing application 53. In addition, the module 50 further includes at least one communications interface to transmit and receive communications, messages, and/or signals.

The module 50 may display on a display a graphical user-interface (or GUI) to generate a graphical user interface on the display. The graphical user interface may be provided by the image processing application 112. The graphical user interface enables a user of the module to interact with the image processing application 53. The GUI may be a component of an application and/or service executable by the module 50. For example, the image processing application 53 may be a single unit of deployable executable code or a plurality of units of deployable executable code.

The image processing application 53 may be a web application, a native application, and/or a mobile application (e.g., an app) downloaded from a digital distribution application platform that allows users to browse and download applications developed with software development kits (SDKs) including the App Store and GOOGLE PLAY®, among others. The image processing application 53 or at least a portion thereof may be resident and executed by the at least one computing device, which may have the WIN- DOWS® operating system, a Linux-based operating system, the OS X® operating system, the iOS operating system, or an ANDROID™ operating system, among other operating systems.

The processor 51 of the image analysis module 50 may including a communication device for communicating data received from the image processing application 53 or memory 52 to a remote computational device 60 via a communications network 44. The remote computational device 60 may be a mobile phone comprising software (i.e. downloadable software in the form of a mobile phone application ("app")) configured to cause the device to communicate with and receive data from the image processing module 50, and display the data. The data may be information about the sample, such as diagnosis of parasitic infection, type of infection, stage of infection, prognosis for animal, and information about suitable treatment. The app may also cause the device to request ID information for the mammal for which a digital image was taken, and associate the mammal ID with the sample data received from the image analysis module, and display the sample data with the mammal ID.

Referring to FIGS. 9A and 9B, an alternative embodiment of the portable digital imaging module is illustrated, in which parts identified with reference to the previous embodiments are assigned the same reference numerals. In the embodiment, the portable digital imaging module 60 does not have a camera or a communications module, but comprises a housing 20 containing a microscopic lens 21B, a seat 23 for receiving a McMaster slide 3 disposed under the lens 21B containing the faecal sample, and a first illumination system 61 disposed under the seat 23, a diffraction filter 62 disposed between seat 23 and first illumination system 61, and a second illumination system 63 positioned laterally of the seat 23. In this embodiment, the housing 20 comprises a cut-out 65 dimensioned to receive an end of a mobile phone 66 having a camera 67 and position the camera so that it is directed towards the seat 23 and lens 21B, in a position to generate digital images of the slide. In this embodiment, the seat 23 is a slot that extends through the housing, and the housing may include means for moving the slide through the slot while digital images are taken of the slide. This allows the generation of digital images covering the whole slide. In this embodiment, the digital images of the sample on the slide are wirelessly communicated to the off-site digital image analysis module by the mobile phone, and the data from the analysis module is received by the mobile phone and displayed in the screen. The module 4 also includes a battery operatively connected to the illumination system.

The embodiment, of FIGS. 9A and 9B allows a simpler kit and system, that can be used with a users own mobile phone or mobile device. In this and other embodiments, the kit and systems of the invention may employ downloadable software for a mobile phone (i.e. a mobile device "app"), which can be configured to perform the method of the invention. For example, the app when run on the operating system of the mobile phone may cause the mobile phone to (a) request ID information for the mammal (b) taken one or a series of digital images of the sample on the slide (c) wirelessly send the digital image(s) to the off-site image analysis module (d) communicate with and receive data (i.e. a parasitic infection characteristic for sample) from the off-site image analysis module and (d) display the parasitic infection characteristic on the screen of the device (optionally with ID data for the mammal). The phone software may also cause the phone to establish communication with the digital imaging module and actuate the illumination systems when the phone is taking a digital image. The phone software may also cause the phone to store parasitic infection characteristics obtained for a mammal over a period of time, and display the parasitic infection characteristics on the phone.

Referring to FIGS. 10A and 10B, an alternative embodiment of the portable digital imaging module is illustrated, in which parts identified with reference to the previous embodiments are assigned the same reference numerals. The digital imaging module 70 has a housing 20 containing a camera 21A, microscopic lens 21B, a slotted seat 23 for receiving a McMaster slide 3 (containing the faecal sample) disposed under the lens 21B, a first illumination system 61 disposed under the seat 23, diffraction filter 62, a second illumination system 63 positioned laterally of the seat 23, and a communications module 71 configured to wirelessly send digital images to a mobile device 66 (not shown). In this embodiment, the module 70 includes a servo motor 72 and rotary actuator 73 positioned to abut a side of the slide 3 in the slotted seat that upon actuation moves the slide laterally along the slotted seat. A second servo motor 74 and rotary actuator 75 is provided to laterally move the camera 21A and lens 21B. Movement of the camera/lens and/or slide allows multiple digital images of the slide to be taken ensuring that images covering the whole slide are generated.

It will be appreciated that the process described in the present disclosure may be implemented using various means. For example, some aspects process described in the present disclosure may be implemented in hardware, firmware, software, or any combination thereof. For a hardware implementation, the processing units, or processors(s) may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A system for on-site determination of a parasitic infection characteristic of a non-human mammal, comprising:
   a portable faecal sample preparation device configured for use on-site to receive faecal matter from the mammal and a faecal flotation fluid, mix the faecal matter and faecal flotation fluid to provide a suspension, and filter the suspension to provide a filtrate, in which the filtrate is the faecal sample;
   a translucent faecal sample support;
   a portable digital imaging module adapted to generate a digital image of a faecal sample on the sample support and communicate the digital image via a wireless communications network by detachable engagement with a mobile communications device in a sample support imaging position, in which the digital image of the faecal sample on the sample support is generated by a camera of the mobile communications device and communicated to the off-site digital image analysis module via the mobile communications device;

an off-site digital image analysis module configured to receive the digital image of the faecal sample via the wireless communication network, analyse the digital image to determine a parasitic infection characteristic of the sample, and communicate the parasitic infection characteristic of the sample via a wireless communications network; and downloadable software for a mobile communications device configured to cause the mobile communications device to:
receive the digital image of the faecal sample;
communicate the digital image to the off-site digital image analysis module;
receive the parasitic infection characteristic of the sample from the off-site digital image analysis module;
request input of identification data for the mammal into the mobile communications device;
receive and store identification data for the mammal;
display on the screen of the mobile communications device the parasitic infection characteristic of the sample, or display on the screen of the mobile communications device the parasitic infection characteristic of the sample and the mammal identification data; and
store a plurality of parasitic infection characteristics for the same mammal obtained over a period of time, and display the plurality of parasitic infection characteristics on the mobile communications device.

2. A system according to claim 1, in which the portable digital imaging module and mobile communications device when assembled comprise:
a camera and lens assembly configured to generate the digital image of the sample on the sample support;
a sample support illumination system;
a seat for receiving the sample support; and
a battery operatively connected to the camera and lens assembly, memory and illumination system.

3. A system according to claim 2, in which the portable digital imaging module is configured for snap-fit attachment to the mobile communications device.

4. A system according to claim 2, in which the portable digital imaging module is adapted to provide relative movement between the sample support and the camera and lens assembly to allow generation of a plurality of digital images across the sample support.

5. A system according to claim 4, in which the portable digital imaging module comprises a seat adjustment module configured for lateral adjustment of the seat relative to the camera and lens assembly upon actuation.

6. A system according to claim 5, in which the seat adjustment module is configured for manual adjustment.

7. A system according to claim 5, including an actuating motor operatively connected to the seat adjustment module.

8. A system according to claim 2, in which the lens is an ultra wide angle lens.

9. A system according to claim 2, in which the camera is configured to generate an ultra-high resolution image of part of the sample slide.

10. A system according to claim 2, in which the seat for the sample support is disposed between the sample support illumination system and camera and lens assembly.

11. A system according to claim 2, in which the illumination system comprises a direct light source disposed under the seat for the sample support, and an indirect light source disposed at one side of the seat for the sample support.

12. A system according to claim 1, in which the off-site image processing module comprises a processor to analyse the digital image by correlating the digital image or a part of the digital image with a characteristic of the faecal sample by comparing the digital image or the part of the digital image with a database of reference images or features from the reference images.

13. A system according to claim 12, in which the processor is configured to analyse the digital image by deep learning.

14. A system according to claim 12 in which the processor comprises a computational model configured to:
receive an input comprising the digital image or features extracted from the digital image, in which the computational model is generated from a training set of digital images of faecal samples of known parasitic infection characteristics; and
output a characteristic of the faecal sample selected from diagnosis of parasitic infection, type of parasitic infection, extent or stage of infection.

15. A method of on-site detection of a parasitic infection of a mammal, comprising the steps of:
preparing on-site a faecal sample for imaging by mixing the faecal sample with a faecal flotation fluid and filtering the faecal flotation fluid through a filter to provide a filtrate, in which the filtrate is the faecal sample;
placing a drop of the faecal sample on a translucent sample support;
generating, on-site, using a camera of a mobile communications device detachably attached to a portable digital imaging module in a sample support imaging position and comprising a communication system adapted to communicate a digital image to an off-site image processing module via a wireless communications network, the digital image of the faecal sample on the sample support;
communicating the digital image, using the communication system of the mobile communications device, to an off-site digital image analysis module via a wireless communication network;
analysing, off-site by the digital image analysis module, the digital image to determine a parasitic infection characteristic of a sample;
communicating the parasitic infection characteristic of the sample via a wireless communications network to the mobile communications device comprising software configured to communicate with, and receive the parasitic infection characteristic of the sample, from the off-site digital image processing module via the wireless communication network;
requesting by the mobile communications device input of identification data for the mammal into the mobile communications device;
receiving and storing by the mobile communications device identification data for the mammal;
displaying by the mobile communications device the parasitic infection characteristic of the sample on the screen of the mobile communications device, or displaying by the mobile communications device the parasitic infection characteristic of the sample and the mammal identification data; and
storing by the mobile communications device a plurality of parasitic infection characteristics for the same mammal obtained over a period of time, and displaying by the mobile communications device the plurality of parasitic infection characteristics over time.

16. A method according to claim 15, in which the portable digital imaging module is adapted to provide relative movement between the sample support and the camera and lens assembly, in which the method includes generation of a plurality of digital images while moving the sample support relative to the camera and lens assembly to generate of a plurality of digital images across the sample support.

17. A method according to claim 15, including a step of illuminating an underside of the sample support with direct light and a side of the sample support with indirect light during the generation of the digital image of the sample support.

18. A method according to claim 15, in which the step of analysing, off-site by the digital image analysis module, the digital image to determine a parasitic infection characteristic of a sample comprises comparing the digital image or the part of the digital image with one or more of a database of references images or features from the reference images to correlate the digital image or a part of the digital image with a characteristic of the faecal sample.

19. A method according to claim 18, in which the digital image is analysed by deep learning.

20. A system according to claim 1, in which the portable faecal sample preparation device comprises:
a vessel with an opening and a detachable closure for the opening of the vessel, wherein the detachable closure comprises a lid and a filter disposed between the opening of the vessel and the lid, wherein the lid is openable and closable; and
optionally, a low-cost paper centrifugation device configured to centrifuge the filtrate.

21. A kit comprising:
a portable faecal sample preparation device configured for use on-site to receive faecal matter from a mammal and a faecal flotation fluid, mix the faecal matter and faecal flotation fluid to provide a suspension, and filter the suspension to provide a filtrate, in which the filtrate is the faecal sample;
a translucent faecal sample support;
a portable digital imaging module comprising a seat for receiving the translucent faecal sample support and a sample support illumination system, the portable digital imaging module configured for detachable engagement with a mobile communications device in a sample support imaging position; and
software for a mobile communications device, the software configured to cause the mobile communications device to:
request ID information for the mammal;
take one or a series of digital images of a faecal sample on the sample support;
communicate the one or the series of digital images to an off-site image analysis module via a wireless communication network for off-site analysis of the digital image to determine a parasitic infection characteristic of the faecal sample;
communicate with, and receive the parasitic infection characteristic of the faecal sample, from the off-site image analysis module via the wireless communication network;
associate the mammal ID with the parasitic infection characteristic received from the image analysis module; and
display the parasitic infection characteristic on the screen of the mobile communications device with the mammal ID.

22. A kit according to claim 21, in which the portable digital imaging module is configured for snap-fit attachment to the mobile communications device.

23. A kit according to claim 21, in which the portable digital imaging module is adapted to provide relative movement between the sample support and a camera of the mobile communications device to allow generation of a plurality of digital images across the sample support.

24. A kit according to claim 23, in which the portable digital imaging module comprises a seat adjustment module configured for lateral adjustment of the seat relative to the camera of the mobile communications device upon actuation.

25. A kit according to claim 24, in which the seat adjustment module is configured for manual adjustment.

26. A kit according to claim 24, including an actuating motor operatively connected to the seat adjustment module.

27. A kit according to claim 21, in which the seat for the sample support is disposed between the sample support illumination system and the camera of the mobile communications device.

28. A kit according to claim 21, in which the illumination system comprises a direct light source disposed under the seat for the sample support, and an indirect light source disposed at one side of the seat for the sample support.

29. A kit according to claim 21, in which the faecal sample support is a McMaster slide.

30. A kit according to claim 21, in which the software is further configured to cause the mobile communications device to store parasitic infection characteristics of the sample for the same mammal obtained over a period of time and display the parasitic infection characteristics over time.

31. A kit according to claim 21, in which the software is downloadable mobile phone application software.

32. A kit according to claim 31, in which the software is configured to cause the mobile communications device to establish communication with the digital imaging module and actuate the illumination systems when the mobile communications device is taking a digital image.

33. A kit according to claim 21, in which the portable digital imaging module further comprises a battery operatively connected to the illumination system.

* * * * *

UNITED STATES PATENT AND TRADEMARK OFFICE
CERTIFICATE OF CORRECTION

| | | |
|---|---|---|
| PATENT NO. | : 12,345,702 B2 | Page 1 of 1 |
| APPLICATION NO. | : 17/413744 | |
| DATED | : July 1, 2025 | |
| INVENTOR(S) | : Sean Smith et al. | |

It is certified that error appears in the above-identified patent and that said Letters Patent is hereby corrected as shown below:

On the Title Page

Item (72), under Inventors please correct 2nd inventor's name:
Tara MCELLIGOTT
To:
Tara MC ELLIGOTT Signed and Sealed this
Twelfth Day of August, 2025

Coke Morgan Stewart
*Acting Director of the United States Patent and Trademark Office*